United States Patent [19]

Hillman et al.

[11] Patent Number: 5,001,290
[45] Date of Patent: Mar. 19, 1991

[54] PRODUCTION OF DICHLOROBENZENE WITH HIGH PARA TO ORTHO RATIOS

[75] Inventors: Melville Hillman, Hilliard; James D. Browning, Columbus, both of Ohio

[73] Assignee: Battelle Memorial Institute, Columbus, Ohio

[21] Appl. No.: 467,332

[22] Filed: Jan. 19, 1990

Related U.S. Application Data

[63] Continuation-in-part of Ser. No. 296,549, Jan. 11, 1989, abandoned.

[51] Int. Cl.$^5$ .................. C07C 17/12; C07C 25/08
[52] U.S. Cl. .................... 570/210; 570/206; 570/207
[58] Field of Search .................. 570/210, 206, 207

[56] References Cited

U.S. PATENT DOCUMENTS

| 1,963,761 | 6/1934 | Prahl et al. | 570/210 |
| 2,527,606 | 10/1950 | Webb | 570/210 |
| 3,029,296 | 4/1962 | White et al. | 570/210 |
| 4,300,004 | 11/1981 | Wissner et al. | 570/210 |
| 4,570,023 | 2/1986 | Petrauck et al. | 570/210 |

FOREIGN PATENT DOCUMENTS

| 2230369 | 1/1973 | Fed. Rep. of Germany | 570/210 |
| 10127 | 5/1965 | Japan | 560/210 |
| 49-76828 | 7/1974 | Japan | 570/210 |

OTHER PUBLICATIONS

Konishi et al.; Regioselective Para-Chlorination of Alkylbenzenes on Chemically Modified Silica Surfaces; Chemistry Letters; 1980; pp. 1423-1426.
Kovacic et al.; Chlorination of Aromatic Compounds with Metal Chlorides; Journal of the American Chemical Society; vol. 76; 11/5/54; pp. 5491-5494.
Wiegandt et al.; Improved Yields of p-Dichlorobenzene; Industrial and Engineering Chemistry; Sep. 1951; pp. 2167-2172.
Hawley (rev.) *The Condensed Chemical Distionary*, New York; Van Nostrand Reinhold Co., 1983 (p. 1081).
CA85; 46467t abstract of Japanese Kokai 74/76,828.

Primary Examiner—Werren B. Lone
Attorney, Agent, or Firm—Klaus H. Wiesmann

[57] ABSTRACT

A method for producing p-dichlorobenzene using a reactor containing a catalyst/reagent to convert chlorobenzene (or benzene) to p-dichlorobenzene, the reactor having an inlet and an outlet for introducing reactants and removing product; introducing a pulse of gaseous chlorobenzene (or benzene) into the reactor and reacting the chlorobenzene with the catalyst/reagent whereby p-dichlorobenzene is formed; introducing a pulse of inert gas into the reactor; introducing a pulse of gaseous chlorine into the reactor and reacting the chlorine with the catalyst/reagent; introducing a pulse of inert gas into the reactor; repeating the pulsing steps in a sequential manner, whereby mixing of the vaporized benzene or chlorobenzene, and the chlorine gas is prevented; and continuously removing product containing p-dichlorobenzene from the outlet of the reactor.

22 Claims, 2 Drawing Sheets

PRODUCTION OF DICHLOROBENZENE WITH HIGH PARA TO ORTHO RATIOS

This is a continuation-in-part of copending application U.S. Ser. No. 07/296,549 filed on Jan. 11, 1989, abandoned.

FIELD OF THE INVENTION

The present invention relates to the production of p-dichlorobenzene by an improved vapor phase process that results in a product mixture with a para/ortho (P/O) ratio in the range of 20/1 to 30/1 or a P/P+O ratio of 95 to 97 percent para at higher efficiency. Sequential, alternating pulses of chlorine gas, inert gas, and chlorobenzene (or benzene) vapors with or without a carrier gas are continuously passed over a catalyst/reagent composition. A novel catalyst/reagent composition is prepared for improved production of p-dichlorobenzene.

BACKGROUND OF THE INVENTION

P-dichlorobenzene is an important raw material for production of polyphenylene sulfide. Various processes for production of p-dichlorobenzene have been developed, however, a simpler process that results in lower costs and high yields is still needed. Conventional commercial processes for chlorinating benzene or monochlorobenzene to dichlorobenzene produce about 3/2 para/ortho (P/O) isomer ratio, and so the efficiency of the processes suffer from inherent limitations because of the large amount of unwanted o-dichlorobenzene produced. An improved process with greater efficiency in which the para/ortho (P/O) isomer ratio is 9/1 or greater is of great utility.

Konishi et al, in *Regioselective Para-Chlorination of Alkylbenzenes on Chemically Modified Silica Surfaces*, Chemistry Letters, 1980, pp. 1423-1426, describe the chlorination of alkylbenzenes with chlorine in carbon tetrachloride in the presence of chemically modified silica catalysts. The silica catalysts showed higher selectivity than $FeCl_3$.

Peter Kovacic et al, *Chlorination of Aromatic Compounds with Metal Chlorides*, Journal of the American Chemical Society, Vol. 76, Nov. 5, 1954, pp. 5491-5494, teach the use of metal chlorides to halogenate aromatic compounds. Chlorination of chlorobenzene with chlorine gas using ferric chloride as a catalyst gave a P/O ratio of about 54 percent. $FeCl_3$ alone gave a ratio of about 88 percent.

Herbert F. Wiegandt et al, in *Improved Yields of p-Dichlorobenzene*, Industrial and Engineering Chemistry, September 1951, pp. 2167-2172, teach the batch and continuous production of dichlorinated benzenes. Effective catalysts were found to be $AlCl_3$, $FeCl_3$, $I_2$, $SbCl_5$, Fe powder, $SnCl_4$; optimum reaction temperatures were determined. Batch chlorination in the liquid phase and continuous chlorination with a uniform suspension of hydrocarbon/catalyst is discussed.

Walter Prahl et al, in U.S. Pat. No. 1,963,761, teaches a process of making chlorobenzene from benzene where dichlorobenzene is also produced; vaporized benzene, hydrogen chloride and oxygen with or without a carrier gas are passed over a contact substance of copper, metals or their compounds (e.g. $FeCl_3$, CuCl).

G. A. Webb, in U.S. Pat. No. 2,527,606, teaches the production of p-dichlorobenzene from benzene. The process uses catalysts such as aluminum chloride, zinc chloride, iron chloride, or metallic fluorides. Approximately equal parts of benzene and monochlorobenzene are added. The benzenes and catalyst flow countercurrent to chlorine in a reactor.

W. A. White et al, in U.S. Pat. No. 3,029,296, conceived of a process in which $FeCl_3$ was used as a reagent but the spent $FeCl_3$ (or $FeCl_2$, ferrous chloride) was moved from the reactor to a chlorinator where it was treated with chlorine to regenerate $FeCl_3$, which was then transported back to the reactor for use again as a chlorinating reagent. This concept provides P/P+O ratios of 92 to 96 percent. However, high costs are involved in solid materials handling. Further other problems involved the transporting of $FeCl_3/FeCl_2$ back and forth between the reactor and chlorinator that resulted in "fines" which tend to cause blockage in the reactor because of the differences in molecular volume (or density) that results from cycling back and forth between $FeCl_3$ and $FeCl_2$.

Adolf Wissner et al, in U.S. Pat. No. 4,300,004, teach the separation of ortho-, meta-. and para-dichlorobenzene from an isomeric mixture thereof.

Japanese patent Kokai 74/76,828 teaches the batch and continuous production of monochlorotoluene. The reaction is in the vapor phase. In the batch system, vaporized toluene contacts with ferric chloride to produce chlorotoluene. When all $FeCl_3$ is consumed, chlorine gas is introduced to regenerate the ferric chloride. When ferric chloride is regenerated toluene is again introduced. In the continuous operation. chlorine gas and toluene are simultaneously reacted over ferric chloride. The process is stated to be applicable to chlorobenzene.

BRIEF DESCRIPTION OF THE INVENTION

The invention includes a method for producing p-dichlorobenzene that comprises the steps of providing a reactor containing a catalyst/reagent adapted to convert chlorobenzene (or benzene) to p-dichlorobenzene, wherein the reactor has an inlet and an outlet for introducing reactants and removing product; introducing a pulse of vaporized chlorobenzene (or benzene) into the reactor and reacting the chlorobenzene (or benzene) with the catalyst/reagent whereby p-dichlorobenzene is formed; introducing a pulse of inert gas into the reactor; introducing a pulse of chlorine gas into the reactor and reacting the chlorine with the catalyst/reagent; introducing a pulse of inert gas into the reactor; repeating the pulsing steps in a sequential manner; and continuously removing product containing p-dichlorobenzene from the outlet of the reactor. The reactor is maintained at a temperature between about 100° C. and about 190° C., and preferably between about 140° C. and about 175° C. Temperatures given here and below are in degrees Centigrade and are designated by the symbol C. It is understood that the symbol C when used with temperatures herein is interchangeable with °C. The $FeCl_3$ or mixture of $AlCl_3$ and $FeCl_3$ used herein functions as a catalyst and reagent. The activated catalytic species is converted to an intermediate during the reaction. The spent catalyst intermediate is then regenerated to the activated form again. Thus, they have been referred to herein as a catalyst or a catalyst/reagent, it is being understood that each term can substitute for the other.

A yet further embodiment of the invention includes a method for producing a composition useful for producing p-dichlorobenzene comprising: Dissolving $FeCl_3$ or a mixture of $FeCl_3$ and $AlCl_3$ in acetone to form a solution; contacting the solution with a porous inert substrate; and depositing the FeCl₃ or the mixture of FeCl₃ and AlCl₃ on the substrate by removing the acetone. A further embodiment includes the step of activating the FeCl₃, or FeCl₃ and AlCl₃ deposited on the substrate by treating the composition with chlorine gas. A final embodiment includes a catalyst/reaction composition for producing p-dichlorobenzene comprising a porous inert substrate having a catalyst/reagent adapted to convert chlorobenzene (or benzene) to p-dichlorobenzene deposited thereon. The porous inert substrate is preferably a resilient material such as vermiculite. The catalyst/reagent is preferably a mixture of FeCl₃ and AlCl₃ although FeCl₃ alone may be used.

A specific embodiment of the invention includes a method for producing an improved catalyst/reagent that comprises dissolving a catalyst/reagent selected from the group consisting of anhydrous ferric chloride, or a mixture of anhydrous ferric chloride and anhydrous aluminum chloride in acetone to form a solution; preparing a slurry of powdered porous inert substrate and acetone; mixing the slurry and solution; and evaporating the acetone from the mixture.

Another embodiment encompasses apparatus for producing p-dichlorobenzene from chlorobenzene that includes a gas supply that provides a source of gaseous chlorine, inert gas, and chlorobenzene; a control and pulse-meter for receiving gases from the gas supply that switches between the sources of gaseous chlorine, inert gas, and chlorobenzene so as to provide pulses of each gas to the input of a reactor column; one or more reactor columns each having an input and an output and a catalyst/reagent composition disposed therein adapted to convert chlorobenzene to p-dichlorobenzene that accepts pulses of gases from the control and pulse-meter at the input; and a separator for separating product gases from the output of the reactor.

DETAILED DESCRIPTION OF THE INVENTION AND PREFERRED EMBODIMENTS

Figure 1:
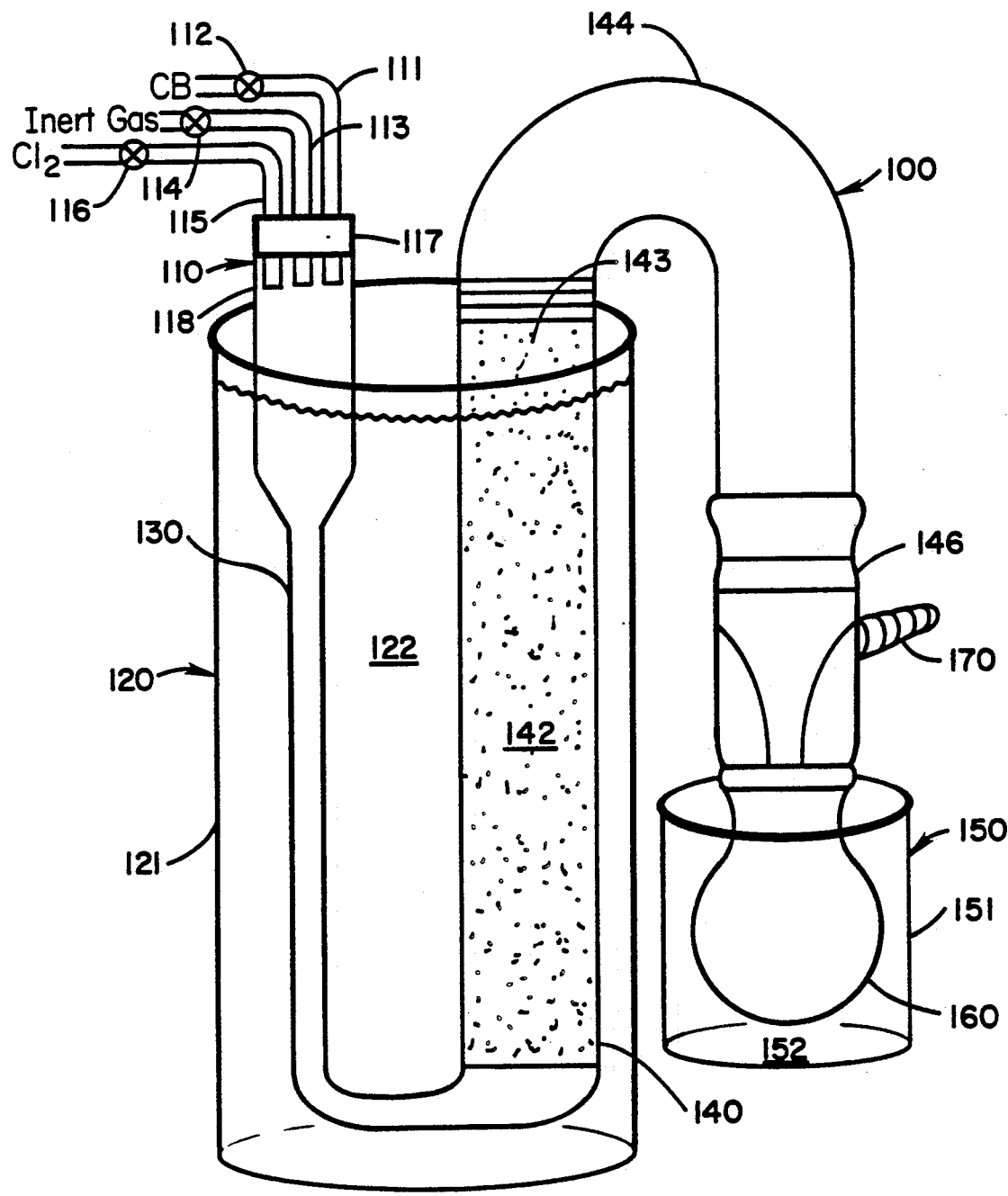
FIG. 1 illustrates an apparatus used for the experiments herein.

An improved process for the chlorination of chlorobenzene for production of dichlorobenzene with a P/O ratio of greater than 9 to 1 is disclosed. The process consistently gives a P/P+O ratio of 95 to 97 percent. This translates to a P/O ratio ranging from 19 to 1 to over 32 to 1. The process has been well demonstrated in a laboratory bench-scale reactor. One novel catalyst composition (FeCl₃+AlCl₃ on vermiculite) was cycled more than 40 times and was still active and producing p-dichlorobenzene in a P/P+O ratio of over 95 percent.

While not wishing to be bound thereby, it is presently believed that there are two separate and entirely distinct mechanisms for the reaction. One involves the chlorination of chlorobenzene with chlorine gas (Cl₂) using a Lewis acid or metal chloride catalyst (e.g., FeCl₃). The second involves the direct chlorination of chlorobenzene with a metal chloride (e.g., FeCl₃).

Simplified equations for these two reactions are:

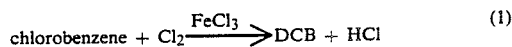

Equation (2B) shows that the FeCl₃ can be regenerated with Cl₂ and therefore the overall stoichiometry for both reactions is the same.

The best proof for this duality of mechanisms is that FeCl₃ can be dissolved in chlorobenzene and does not react until it is heated to about 125° C. or higher. However, if chlorine is added to FeCl₃ dissolved in chlorobenzene (CB) solution, immediate reaction occurs at room temperature or lower.

We believe the mechanisms and transition states can be simply illustrated by the equations:

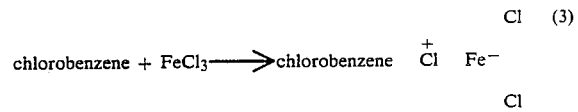

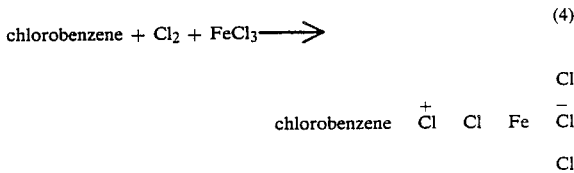

It can be seen from the formulas on the right of these equations that the bulky iron group is much closer to the chlorobenzene molecule in formula (3) than in formula (4). Also, the iron atom in formula (3) is additionally complexed to at least one other iron atom, that is not shown in the diagram, so the steric hindrance is much greater than indicated. While FeCl₃ and AlCl₃ are actually complexed to other FeCl₃ and AlCl₃ molecules, the complex of catalyst/reagent will be referred to as FeCl₃, and a mixture of FeCl₃ and AlCl₃ for purposes of discussion herein.

Another way of describing this difference is that in the FeCl₃ catalyzed formula (4) the bulky iron group is one more atomic distance removed from the chlorobenzene molecule than for the FeCl₃ reagent formula (3). This means that steric hindrance to ortho substitution is significantly more important in the ferric chloride-reagent reaction. It appears that one cannot create an equivalent amount of steric hindrance with a catalyzed system and get a similar high P/P+O ratio. The problem then becomes one of how to make the reagent process behave as if it is a catalytic process.

Gas Chromatography Analytical Procedure

A gas chromatographic method for analyzing the reaction product mixtures resulting from the chlorination of chlorobenzene was used. The instrument used for these chromatographic analyses was a Varian 2100 with hydrogen flame ionization detector. A silane treated glass column (6 ft×4 mm ID) packed with 10 percent Carbowax 20M-TPA on 80/100 Chromosorb W-AW, was used to separate the different reaction compounds and a Hewlett Packard (3390A) integrator was used for measuring peak areas.

In general, the flow rate (30 mls/min) of the carrier gas ($N_2$) and the column temperature (130° C. isothermal for 30 mins) were optimized to provide baseline resolution for the simultaneous analyses of chlorobenzene, m-dichlorobenzene, p-dichlorobenzene, o-dichlorobenzene and trichlorobenzene.

After optimization of chromatographic conditions a series of standards, varying in concentration over the linear range, were prepared by serial dilution and analyzed in duplicate.

Standard curves were established by plotting concentration (g/ml) versus peak area and slopes for the resulting straight lines were determined. Additionally, standards were analyzed at the same time as the reaction mixtures since no internal standard was incorporated. This permitted correction for variation in flame ionization detector response with time.

Typically, aliquots of reaction mixtures were taken at about 30 minute intervals throughout the course of the reaction and analyzed by chromatography.

The resulting areas for the compounds obtained from the integrator were entered onto an IBM-PC with 20 megabyte hard disc. A program was developed using Lotus 1-2-3, to convert the peak areas obtained from the integrator into mole percent of reactants and products formed during the chlorination reactions. The slopes from the standard curves for each compound and the dilution factors for each sample were also entered into the computer program and used in the ensuing calculations.

Referring now to FIG. 1, the laboratory scale vapor phase reactor 100 used in proving the efficacy of the invention includes input means 110, oil bath 120, vaporizer 130, reactor 140, and product separator 150. In operation input gases comprising chlorobenzene, inert carrier gas, and chlorine entered by pipes 111, 113, 115 respectively. Flow for these gases was controlled by valves 112, 114, and 116. Stopper 117 provided support for piping and sealed the apparatus. The oil bath 120 consisted of a large beaker 121 filled with silicone oil 122 and provided for heat for the vaporizer 130 to assure that any liquid was vaporized and that only gas was inputed at reactor 140. Another function of the oil bath was to regulate the temperature of the reaction in reactor 140. The reactor 140 was filled with catalyst/reagent comprising $FeCl_2$ and $AlCl_2$ preferably deposited on vermiculite or a like inert substrate as further described below to form a catalyst bed 142.

Elbow 144 connected the output 143 of the reactor 140 to a T-fitting 146 that connected to a product collector 150. Product collector 150 comprises a beaker 151 containing an ice bath 152 and round bottom flask 160 connected to the bottom of T-fitting 146. Gases such as inert gas and HCl that are not collected in flask 160 exit at outlet 170.

For the examples herein, typically a reagent quantity (25-80 g) of catalyst (i.e., $FeCl_3$) was loaded into a vapor phase reactor 140 (0.2 liter). The reactor 140 was immersed in a hot oil bath 120 and equilibrated to the desired reaction temperature (160° C., nominal). Prior to entering the reaction zone chlorobenzene was pumped (via syringe pump) through a vapor tube under a stream of argon to enhance chlorobenzene vaporization. The argon stream also served to carry the reaction products up through the catalyst bed 142 into an ice-bath cooled receiver 160 (see FIG. 1).

After addition of chlorobenzene the catalyst bed 142 was flushed with argon and rechlorinated with $Cl_2$ by passing the gases through calibrated rotometers and up through the catalyst bed for specific time periods.

Thus, the sequence of activities for most of the vapor phase experiments was:
1. $Cl_2$ feed (initial chlorination if needed);
2. Argon flush;
3. CB feed;
4. Argon flush;
5. $Cl_2$ feed; and
6. Argon flush.

At the end of each experiment the receiver was changed and the contents analyzed by vapor phase chromatography. The next experiment was started immediately or the reactor was cooled by 20-40° C. and placed under a slow stream of argon (10-20 ml/min) overnight.

The experimental runs that involved pulsed flow vapor phase conditions include Experiments 1, 2, 3, and 4. These experiments are summarized in Tables 1 A-B, 2 A-B, 3 A-E, and 4 A-B respectively.

The most important and comprehensive studies for demonstrating the pulsed flow concept are Experiments 3 and 4. In these two experiments all of the samples were reacted with the same catalyst bed.

EXAMPLES 1-8

Acronyms used in the tables, examples, and discussion herein have the following definitions:
CB - chlorobenzene
MDBC - meta-dichlorobenzene (m-dichlorobenzene)
PDBC - para-dichlorobenzene (p-dichlorobenzene)
ODBC - ortho-dichlorobenzene (o-dichlorobenzene)
TCB - trichlorobenzene Experiment 1 consisted of a series of initial vapor phase experiments. The catalyst bed was neat anhydrous. $FeCl_3$ fine crystals 98 percent (Aldrich Cat. No. 15,7740) (71.2 g. 0.439 moles). In this reactor the flow of gases was down through the catalyst bed. The chlorobenzene was vaporized by dripping it down onto a 2 cm thick layer of glass beads in the top part of the reactor (above the catalyst bed).

The results for Experiment 1 are summarized in Tables 1A and 2B. In examples 1 and 2 chlorine gas and chlorobenzene vapors were fed simultaneously through the catalyst bed. In example 1 the catalyst bed had been exhaustively chlorinated prior to the reaction to assure that it was in the $FeCl_3$ form. The conversion was about 76 percent and the P/P+O ratio was about 82 percent.

For example 2 the catalyst bed had not been regenerated and was predominantly in the $FeCl_2$ form. In this case, the conversion was only about 36 percent and the P/P+O only 67 percent. This drop in both conversion and P/P+O ratio indicates that in example 1 catalytic ($Cl_2$ gas) and reagent ($FeCl_3$) reactions are both occurring simultaneously.

In the next six examples (3-8) the chlorine and chlorobenzene were fed at different times (not simultaneously) and the most important observation to make is that the P/P+O ratio increased to the range of 92.3 to 97 percent. In fact, after the initial reaction (example 3) the next five examples had an average P/P+O value of 96.3 percent; this is a P/O ratio of 26/1.

In comparing all eight examples in this series (1-8), it should be noted that not only is the P/P+O ratio much smaller when the chlorine and chlorobenzene are fed simultaneously but the amount of trichlorobenzene produced is also much higher (2.1 to 6.2 percent). With separate feed times for chlorine and chlorobenzene, only trace amounts of trichlorobenzene were formed.

Toward the end of this series of eight examples, blockage or restricted flow of the reactor bed became a problem. In addition, leakage from the test apparatus was noted in several examples as noted in Tables 1A and 1B. The leakage appeared to be caused by high pressures produced by blockage. The blockage appeared to be caused by packing due to the alternate expansion and contraction of the $FeCl_3/FeCl_2$ reactor bed as it went through its cycles. A catalyst support, from a porous inert support such as vermiculite, was prepared to solve this problem. While a porous inert support would be sufficient to provide a large surface area and to prevent blockage a porous inert and resilient support is presently preferred. The resilience of the catalyst support would further help prevent blockage due to expansion and contraction of the deposited $FeCl_3/FeCl_2$ catalyst/reagent.

tals (Aldrich Cat. No. 15,7740) and anhydrous aluminum chloride (5 grams) in 400 mls of acetone. A slurry of regular vermiculite, packing grade, 1-4 mm particle size, (50 grams) and acetone 300 mls was prepared. The $FeCl_3/AlCl_3$ solution was added to the vermiculite slurry in a 2 liter round bottom flask with a ground glass joint. The flask was attached to a rotor evaporator (Rotovac ®) and the acetone was stripped off with a water aspirator. When most of the acetone was removed the flask was heated in a hot water bath to about 85° C. to give 126.3 grams of the catalyst. Some of this catalyst (66 2 grams containing 26.2 grams of $FeCl_3$) was charged to the reactor that was immersed in a silicone oil bath heated to about 160° C. Argon (20 ccs/min) was passed through the hot reactor for about 24 hours. The catalyst of example 9 was used throughout the rest of the examples.

Kovacic has demonstrated and we have verified that the addition of a small amount (about 5 percent) of $AlCl_3$ to $FeCl_3$ lowers the reaction temperature and also

TABLE 1A

CONTINUOUS VAPOR PHASE CHLORINATION OF CHLOROBENZENE

| Example | Chlorinating Reagents | Reaction Time (mins) | Temp. (C.) | Feed Rate (mls/min) | Total CB Charge (g) | Product Recovered (g) |
|---|---|---|---|---|---|---|
| 1 | $FeCl_3$ + $Cl_2$ | 79 | 168 | CB = 0.54 $Cl_2$ = 56 | 47.6 14.0 | 55.3 |
| No regeneration 2 | $FeCl_2$ + $Cl_2$ | 88 | 168 | CB = 0.52 $Cl_2$ = 37 | 50.9 10.3 | 58.0 |
| Regeneration to $FeCl_3$ 3 | $FeCl_3$ | 69 | 160 | CB = 0.68 $Cl_2$ = 0 | 52.0 | 59.9 |
| Regeneration to $FeCl_3$ 4 | $FeCl_3$ | 56 | 158 | CB = 0.71 $Cl_2$ = 0 | 44.3 | 56.1 |
| No regeneration 5 | $FeCl_2$ | 64 | 155 | CB = 0.73 $Cl_2$ = 0 | 52.0 | 49.9[a] |
| Regeneration to $FeCl_3$ 6 | $FeCl_3$ | 66 | 157 | CB = 0.67 $Cl_2$ = 0 | 48.7 | 53.3 |
| Regeneration to $FeCl_3$ 7 | $FeCl_3$ | 35 | 160 | CB = 0.66 $Cl_2$ = 0 | 25.5 | 22.4[a] |
| No regeneration 8 | $FeCl_2$ | 43 | 160 | CB = 0.58 $Cl_2$ = 0 | 27.7 | 28.6[a] |

[a] Small leaks in the apparatus occurred during these runs. These leaks were due to build up of pressure due to restricted flow resulting from expansion and contraction of the catalyst bed.

TABLE 1B

CONTINUOUS VAPOR PHASE CHLORINATION OF CHLOROBENZENE

| Example | Product Analysis (Mole %) | | | | | CB Conversion % | P/P + 0 Ratio |
|---|---|---|---|---|---|---|---|
| | CB | MDCB | PDCB | ODCB | TCB | | |
| 1 | 24.2 | 0.9 | 56.3 | 12.5 | 6.2 | 75.8 | 81.9 |
| 2 | 64.4 | 1.0 | 21.7 | 10.7 | 2.1 | 35.6 | 66.9 |
| 3 | 65.6 | 0.2 | 31.5 | 2.6 | 0.2 | 34.5 | 92.3 |
| 4 | 68.7 | 0.1 | 29.8 | 1.3 | — | 31.3 | 95.8 |
| 5 | 93.4 | — | 6.4 | 0.2 | — | 6.6 | 96.5 |
| 6 | 67.4 | — | 31.4 | 1.2 | — | 32.6 | 96.3 |
| 7 | 58.2 | 0.1 | 40.0 | 1.7 | — | 41.8 | 96.0 |
| 8 | 80.2 | — | 19.3 | 0.6 | — | 19.8 | 97.0 |

EXAMPLE 9: CATALYST PREPARATION

A novel catalyst was made by depositing an acetone solution of $FeCl_3$ and $AlCl_3$ on vermiculite. The catalyst/reagent was prepared by dissolving 50 grams of anhydrous ferric chloride ($FeCl_3$), 98 percent, fine crysincreases the P/P+O ratio. For example, we found that reaction temperature was lowered from about 155 to about 125° C. and the P/P+O ratio was increased from about 92 to about 96 percent.

Both of these benefits have been realized by codepositing $FeCl_3$ and $AlCl_3$ on a suitable catalyst support. At the reaction temperature of about 160° C. the reaction of chlorobenzene with $FeCl_3/AlCl_3$ is very fast and is all converted to p-dichlorobenzene with minor amounts of o-dichlorobenzene, m-dichlorobenzene and trichlorobenzene before the chlorine reaches that part of the reactor. It has been shown above that if chlorine and chlorobenzene vapor are introduced simultaneously in the reactor the P/P+O ratio drops from about 95 percent to about 70 percent. The catalytic reaction of $Cl_2+FeCl_3$ catalyst occurs at room temperature and is very rapid at 160° C.. (If the $FeCl_3$ catalyst is unmodified, it gives a P/P+O of 59 percent). As indicated above the reaction of chlorobenzene with $FeCl_3$ occurs at 155° C. with a P/P+O of about 92 percent, and the reaction of chlorobenzene with $FeCl_3/AlCl_3$ occurs at 125° C. with a P/P+O of about 96 percent. This means that at 160° C. the reaction of chlorobenzene with FeCl₃/AlCl₃ is essentially instantaneous so that the possibility of chlorobenzene and chlorine molecules coming together in the pulsed flow system even with very short inert gas flow times is greatly reduced. The reaction of $Cl_2$ with $FeCl_2$ is also very rapid at 160° C. Lowering the temperature may require an increase in pulse time for the inert gas. The appropriate length can easily be determined by those skilled in the art. Thus, the short pulse of inert gas can effectively separate the chlorine and benzene or chlorobenzene so as to obtain the benefits of the invention.

Examples 1-8 demonstrated the need for a porous inert or a porous inert resilient (e.g. compressible and expandable) catalyst/reagent substrate. This substrate can be any material such as vermiculite that is porous and has a high surface area, is inert to the reactants used in the process and accepts and retains the catalyst/reagent. The substance preferably compresses and expands when pressure is increased and reduced. The substrate should preferably have a high loading capacity. This loading capacity is enhanced by porosity of the substrate or by rough surface texture. The presently preferred substrate is vermiculite. Further, the vermiculite is preferably a powder having an average particle size of about 1 mm to about 6 mm. Most preferred is an average particle size of about 3 mm. An advantage of vermiculite and the like is that a high degree of loading of catalyst/reagent can be obtained. For example, about 50 weight percent of the catalyst/reagent composition when using vermiculite was catalyst/reagent. This is attributed to the high porosity of the vermiculite.

While an acetone solvent has been used herein, other like solvents may be used. For example lower alcohols such as ethyl alcohol, methyl alcohol, propyl alcohol, and butyl alcohol; and ethers such as diethyl ether and the like may be used.

While a mixture of FeCl₃ and AlCl₃ deposited on vermiculite is demonstrated herein, satisfactory results can be obtained by the use of FeCl₃ alone. Thus process conditions can be modified by those skilled in the art to obtain high yields by the use of FeCl₃ that is also deposited on vermiculite. It is believed that addition of AlCl₃ acts as a catalyst activator and enhances the rate of the reaction.

EXAMPLES 10-16

The results of Experiment 2 of seven examples are summarized in Table 2A and 2B. The catalyst/reagent bed was not treated with chlorine before examples 10 and 11 were carried out and no products were formed. This indicates that the metal chlorides were hydrolyzed or formed stable and unreactive hydrates during the catalyst preparation.

Chlorination with excess chlorine converted the material to an active catalyst bed that gave a P/P+O ratio of 95.8 percent and a 33 percent conversion of 10 ml of chlorobenzene.

Example 13 was carried out without reactivation with chlorine but less than 1 percent conversion was obtained. This indicates that all of the available FeCl₃ was consumed in example 12. Similar sequences were carried out for the remaining three examples as summarized in Tables 2A and 2B.

TABLE 2A

| CHLORINATION OF CHLOROBENZENE WITH FeCl₃ + AlCl₃/VERMICULITE | | | | | |
|---|---|---|---|---|---|
| Example | Chlorinating Reagents | React. Time (mins) | Temp. (C.) | Product Recovery (g) | Weight % Recovery |
| 10* | 50.4 g of FeCl₃/AlCl₃ on Vermiculite | 26 | 168 | 10.5 | 94.9 |
| No regeneration 11* | FeCl₃/AlCl₃ on Vermiculite | 26 | 168 | 10.3 | 93 |
| Regeneration to FeCl₃ 12* | FeCl₃/AlCl₃ on Vermiculite | 25 | 168 | 8.8 | 79.5 |
| No regeneration 13* | FeCl₃/AlCl₃ on Vermiculite | 33 | 165 | 10.54 | 95.2 |
| Regeneration to FeCl₃ 14* | FeCl₃/AlCl₃ on Vermiculite | 29 | 168 | 9.7 | 87.6 |
| No regeneration 15* | FeCl₃/AlCl₃ on Vermiculite | 30 | 172 | 9.84 | 88.9 |
| Regeneration to FeCl₃ 16** | FeCl₃/AlCl₃ on Vermiculite | 16 | 158 | 4.28 | 77.3 |

Feed Rate 0.34 mls/min.
*chlorobenzene charge 10 mls, 0.098 moles, 11.7 g.
**chlorobenzene charge 5 mls, 0.049 moles, 5.54 g.

TABLE 2B

| CHLORINATION OF CHLOROBENZENE WITH FeCl₃ + AlCl₃/VERMICULITE | | | | | | | |
|---|---|---|---|---|---|---|---|
| | Product Analysis (Mole %) | | | | | | |
| Example | CB | MDCB | PDCB | ODCB | TCB | CB Conversion % | P/P + 0 Ratio |
| 10* | 100 | 0 | 0 | 0 | 0 | 0 | — |
| 11* | 100 | 0 | 0 | 0 | 0 | 0 | — |

TABLE 2B-continued

CHLORINATION OF CHLOROBENZENE WITH FeCl₃ + AlCl₃/VERMICULITE

Product Analysis (Mole %)

| Example | CB | MDCB | PDCB | ODCB | TCB | CB Conversion % | P/P + 0 Ratio |
|---|---|---|---|---|---|---|---|
| 12* | 67.3 | 0.3 | 31.0 | 1.4 | ND | 32.7 | 95.8 |
| 13* | 99.3 | ND | 0.7 | ND | ND | 0.7 | 100 |
| 14* | 59.6 | 0.3 | 38.4 | 1.8 | ND | 40.4 | 95.6 |
| 15* | 97.9 | 0 | 1.9 | 0.1 | ND | 2.1 | 93.7 |
| 16** | 11.4 | 0.3 | 84.9 | 3.4 | ND | 88.6 | 96.2 |

ND - not detected
Feed Rate 0.34 mls/min.
*chlorobenzene charge 10 mls, 0.098 moles, 11.7 g.
**chlorobenzene charge 5 mls, 0.049 moles, 5.54 g.

In Examples 17-39 summarized in Tables 3 A-E (Experiment 3) the top half of each table shows the analytical results and the bottom half shows a variety of reaction results and conditions for each example. During the first ten examples (17 to 26) the argon flush, after the chlorobenzene addition was complete, was usually about 30 minutes or more because during these experiments no attempt was made to reduce the total cycle time to a minimum.

EXAMPLES 17-19

These examples show the effect of addition rate on reaction conversion. In examples 17-19 the chlorobenzene addition time is reduced in steps from 28 minutes to 4 minutes with a corresponding drop in conversion from 80 percent to 70 percent. Although the conversion decreased by 10 percent the P/P+O ratio for these experiments remained constant between 95.2 and 95.7 percent.

TABLE 3A

EFFECT OF ADDITION RATE ON CONVERSION (CHLORINE)

| Example No. | 17 | 18 | 19 |
|---|---|---|---|
|  | Mole Percent | | |
| CB | 19.9 | 28.0 | 29.6 |
| MDCB | 0.0 | 0.3 | 0.2 |
| PDCB | 76.4 | 68.3 | 67.1 |
| ODCB | 3.7 | 3.5 | 3.0 |
| TCB | 0.0 | 0.0 | 0.0 |
| % Conversion | 80.1 | 72.0 | 70.4 |
| P/(P + 0) (%) | 95.3 | 95.2 | 95.7 |
| Pro. Rec. Wt. % | 85.2 | 101.4 | 113.7 |
| Cl₂ (mMole) | 301 | 362 | 368 |
| Ar Flush (min) | 30 | 15 | 30 |
| CB (mMole) | 68.8 | 68.8 | 68.8 |
| CB (min) | 28 | 6 | 4 |
| Ar Flush (min) | ≧30 | ≧30 | ≧30 |
| Wt. % Conv. | 84.0 | 77.1 | 75.6 |
| Temp. | 152 | 157 | 156 |

EXAMPLES 20-22

In examples 20, 21, and 22 the corresponding argon flush times are 60, 30 and 16 minutes respectively and the corresponding mole percent conversions are 83, 81, and 75 percent. These examples indicate that when you increase the addition time of the flushes the percent conversion increases.

The same results could be obtained with higher inert gas flows in a shorter time period. The effect appears to be due to the flushing and separation of the reactant gases.

TABLE 3B

EFFECT OF FLUSH TIME ON CONVERSION (ARGON)

| Example No. | 20 | 21 | 22 |
|---|---|---|---|
|  | Mole Percent | | |
| CB | 17.0 | 19.3 | 14.0 |
| MDCB | 0.2 | 0.2 | 0.3 |
| PDCB | 79.4 | 76.9 | 81.3 |
| ODCB | 3.3 | 3.5 | 4.4 |
| TCB | 0.0 | 0.0 | 0.0 |
| % Conversion | 83.0 | 80.7 | 75.4 |
| P/(P + 0) (%) | 96.0 | 95.6 | 94.9 |
| Pro. Rec. Wt. % | 94.0 | 128.4 | 112.1 |
| Cl₂ (mMole) | 374 | 362 | 380 |
| Ar Flush (min) | 60 | 30 | 16 |
| CB (mMole) | 49.1 | 49.1 | 49.1 |
| CB (min) | 3 | 4 | 3 |
| Ar Flush (min) | ≧30 | ≧30 | ≧30 |
| Wt. % Conv. | 86.4 | 84.5 | 80.0 |
| Temp. | 155 | 157 | 155 |

EXAMPLES 23-26

These examples (including Example 22) illustrate optimized catalyst bed regeneration. Examples 22-26 were run to determine the optimum (minimum) amount of chlorine required to regenerate the catalyst bed. The chlorine flow, estimated at 6 millimoles per minute, was decreased in steps from 362 to 45 millimoles. The corresponding chlorine flow times were 60, 45, 30, 15 and 7.5 minutes. The mole percent conversion of chlorobenzene remained relatively constant at 80percent for these experiments but dropped to 67 percent when the chlorine was reduced to 45 millimoles (7.5 mins). Note that the P/P+O ratio remained at the high level of 95.3 percent to 96.4 percent during this series of experiments. The results show that between 45 and 90 millimoles of chlorine are required to regenerate the catalyst bed when the chlorobenzene pulse is 49.1 millimoles. This is good agreement with the theoretical stoichiometric requirement.

TABLE 3C

CATALYST BED REGENERATION

| Example No. | 23 | 24 | 25 | 26 |
|---|---|---|---|---|
|  | Mole Percent | | | |
| CB | 19.2 | 17.5 | 18.8 | 32.9 |
| MDCB | 0.5 | 0.2 | 0.2 | 0.0 |
| PDCB | 76.5 | 78.3 | 75.1 | 63.1 |
| ODCB | 3.7 | 3.8 | 3.3 | 2.4 |
| TCB | 0.0 | 0.2 | 2.6 | 1.6 |
| % Conversion | 80.8 | 82.5 | 81.2 | 67.1 |
| P/(P + 0) (%) | 95.3 | 95.4 | 95.8 | 96.4 |
| Pro. Rec. Wt. % | 112.1 | 103.1 | 121.2 | 104.9 |
| Cl₂ (mMole) | 271 | 181 | 90 | 45 |
| Ar Flush (min) | 30 | 30+ | 25 | 30 |
| CB (mMole) | 49.1 | 49.1 | 49.1 | 49.1 |

TABLE 3C-continued

| | CATALYST BED REGENERATION | | | |
|---|---|---|---|---|
| | 23 | 24 | 25 | 26 |
| Example No. | | Mole Percent | | |
| CB (min) | 4 | 4 | 4 | 4 |
| Ar Flush (min) | ≧30 | ≧30 | ≧30 | ≧30 |
| Wt. % Conv. | 84.6 | 86.0 | 85.0 | 72.8 |
| Temp. | 165 | 157 | 157 | 157 |

EXAMPLES 27–33

The following examples were used to minimize the time for the pulse flow sequence. Examples 27–29 show the results for running a series of pulse-flow experiments that have a total cycle time of 29 minutes. This time consisted of 10 minutes of chlorine feed (at 135 mls/min), an argon flush of 5 minutes, a chlorobenzene (5 mls) feed time of 4 minutes, and an argon flush of 10 minutes. In this set of experiments the percent conversion ranged from about 75 to about 83 percent and the P/P+O ratio remained very stable, ranging from about 95.9 to about 96.3 percent (average=about 96.1, which is a P/O ratio of about 25).

At this point the total cycle time was reduced from 29 minutes down to 17 minutes. This was done by reducing the argon flush time (after chlorine) from 5 to 2 minutes and the argon flush time (after chlorobenzene) from 10 minutes to 1 minute. This effect is demonstrated in examples 30–33. Although the P/P+O remains relatively constant between 96.4 and 95.3 percent, the percent conversion drops continuously from 84 percent for example 30 down to just over 50 percent for example 33.

TABLE 3D

| | MINIMIZATION OF PULSE FLOW TIMES | | | | | | |
|---|---|---|---|---|---|---|---|
| | 27 | 28 | 29 | 30 | 31 | 32 | 33 |
| Example No. | | | | Mole Percent | | | |
| CB | 22.1 | 24.7 | 17.1 | 15.7 | 28.1 | 32.1 | 49.5 |
| MDCB | 0.3 | 0.4 | 0.6 | 0.3 | 0.3 | 0.0 | 0.0 |
| PDCB | 73.0 | 70.2 | 78.4 | 78.6 | 66.6 | 64.0 | 46.2 |
| ODCB | 3.0 | 3.0 | 3.0 | 3.0 | 2.6 | 2.4 | 2.3 |
| TCB | 1.7 | 1.8 | 0.9 | 2.4 | 2.5 | 1.5 | 2.0 |
| % Conversion | 77.9 | 75.3 | 82.9 | 84.3 | 71.9 | 67.9 | 50.5 |
| P/(P + 0) (%) | 96.0 | 95.9 | 96.3 | 96.4 | 96.2 | 96.4 | 95.3 |
| Pro. Rec. Wt. % | 106.7 | 101.3 | 92.2 | 104.9 | 66.9 | 99.5 | 65.1 |
| Cl₂ (mMole) | 60 | 60 | 60 | 60 | 60 | 60 | 60 |
| Ar Flush (min) | 5 | 5 | 5 | 30 | 2 | 2 | 2 |
| CB (mMole) | 49.1 | 49.1 | 49.1 | 49.1 | 49.1 | 49.1 | 98.2 |
| CB (min) | 4 | 4 | 4 | 4 | 4 | 5 | 5 |
| Ar Flush (min) | 10 | 10 | 10 | 1 | 1 | 1 | 1 |
| Wt. % Conv. | 82.3 | 80.0 | 86.4 | 87.6 | 77.1 | 73.5 | 57.4 |
| Temp. | 158 | 158 | 158 | 165 | 165 | 165 | 165 |

EXAMPLES 34–38

These examples illustrate the effect of Cl₂ concentration. To determine the cause of this reduction, the catalyst bed was regenerated with excess chlorine (example 34) and then a series of reactions was carried out (examples 35–38) using about 50 percent more chlorine (89 mMoles) than used in examples 30–33. The higher chlorine content was achieved by increasing the flow rate, not the flow time. In this series the conversion of chlorobenzene to products remained relatively constant between 71 and 77 percent, and the P/P+O ratio remained constant between 95.4 and 96 percent. This indicates that the decline in conversion in examples 30 to 33 was due primarily to insufficient chlorine and not to a build up of heat. In these experiments, there was no lapse of time between each experiment. Thus in examples 34–38, each experiment took 17 minutes and was immediately followed by the next experiment, so that the entire sequence of five experiments took 85 minutes (5×17), at which time the sequence was stopped and the samples were analyzed.

EXAMPLE 39

Because of the variation in the weight of product recovered and the concern that some product could be lost while sample receivers were being changed, in example 39 five separate cycles of the reactor were carried out with all samples collected in the same receiver. The values in Table 3E, example 39 are cumulative values for the five separate cycle samples. For this series the conversion was a high value of 88.5 mole percent or 91.1 weight percent and product recovery weight was good (107.1 percent) but the P/P+O ratio had dropped to 92.9 percent. The reason for this slight drop off is not known.

TABLE 3E

| | 34 | 35 | 36 | 37 | 38 | 39 |
|---|---|---|---|---|---|---|
| Example No. | | | Mole Percent | | | |
| CB | 24.1 | 23.1 | 24.6 | 29.2 | 28.3 | 11.5 |
| MDCB | 0.3 | 0.3 | 0.3 | 0.3 | 0.3 | 0.0 |
| PDCB | 71.6 | 72.0 | 70.3 | 66.5 | 67.2 | 79.2 |
| ODCB | 3.0 | 3.0 | 3.4 | 2.8 | 2.9 | 6.1 |
| TCB | 1.1 | 1.6 | 1.5 | 1.3 | 1.3 | 3.2 |
| % Conversion | 75.9 | 76.9 | 75.4 | 70.8 | 71.7 | 88.5 |
| P/(P + 0) (%) | 96.0 | 96.0 | 95.4 | 95.9 | 95.9 | 92.9 |
| Pro. Rec. Wt. % | 94.0 | 92.2 | 110.3 | 106.7 | 97.6 | 107.1 |
| Cl₂ (mMole) | 179 | 89 | 89 | 89 | 89 | 446 |
| Ar Flush (min) | 30 | 2 | 2 | 2 | 2 | 10 |
| CB (mMole) | 49.1 | 49.1 | 49.1 | 49.1 | 49.1 | 245.6 |
| CB (min) | 4 | 4 | 4 | 4 | 4 | 20 |
| Ar Flush (min) | 1 | 1 | 1 | 1 | 1 | 5 |
| Wt. % Conv. | 80.5 | 81.4 | 80.1 | 76.1 | 76.8 | 91.1 |
| Temp. | 158 | 158 | 158 | 158 | 158 | 165 |

EXAMPLES 40–44

These examples from Experiment 4 show the effect of carrier gas flow rate for this pulse flow system. Instead of separate argon flushes argon was used as a carrier gas during the entire reactions. Experiment 4 was actually a continuation of Experiment 3 in that the same reactor and catalyst charge was used, i.e., FeCl₃+AlCl₃ on vermiculite. In Experiment 4, examples 40–44 each consisted of three separate reactions or pulses all collected in the same receiver, much like Experiment 3, example 39.

Each of examples 40–44 involved a continuous argon flow during the experiment. At the end of the chlorine addition and at the end of the chlorobenzene addition only the argon was allowed to flow (carrier gas) for a period of 30 seconds. The sequence of events for each cycle can be illustrated as:

1. $Cl_2$ flow of 200 ml/min for 10 minutes plus simultaneous argon flow;
2. Only argon flowing for 30 seconds;
3. Chlorobenzene flow (5 mls) for 4 minutes plus simultaneous argon flow;
4. Only argon flowing for 30 seconds; and
5. Repeat step 1 etc. for 3 complete cycles.

The complete cycle time for these experiments was 15 minutes.

At the end of example 40 the sample receiver was changed and example 41 was started. During example 40 the argon flow rate was 100 ml/min. In examples 41–44 the carrier gas flow rate (argon) was 50, 25, 10 and 0 ml/min respectively.

From Table 4A it appears that the optimum argon flow rate under the experimental conditions employed is 25 ml/minute. Although a high flow of carrier gas (100 ml/min) surprisingly resulted in a high conversion (93.4 mole percent) large amounts of ODCB and TCB were also produced. When no carrier gas was used (example 44) the conversion was 100 percent but the TCB formed was very high (36.3 percent). These results are attributed to the longer residence times.

TABLE 4A
EFFECT OF CARRIER GAS FLOW RATE

| Example No. | 40 | 41 | 42 | 43 | 44 |
|---|---|---|---|---|---|
| | Mole Percent | | | | |
| CB | 6.6 | 19.0 | 22.9 | 22.7 | 0.0 |
| MDCB | 0.0 | 0.0 | 0.0 | 0.0 | 0.0 |
| PDCB | 79.6 | 71.9 | 71.0 | 70.9 | 62.4 |
| ODCB | 6.8 | 5.2 | 3.3 | 3.3 | 1.3 |
| TCB | 6.9 | 4.0 | 2.8 | 3.1 | 36.3 |
| % Conversion | 93.4 | 81.0 | 77.1 | 77.3 | 100.0 |
| P/(P + O) (%) | 92.1 | 93.3 | 95.5 | 95.5 | 98.0 |
| Pro. Rec. Wt. % | 103.1 | 104.9 | 95.8 | 94.6 | 88.6 |
| $Cl_2$ (mMole) | 268 | 268 | 268 | 268 | 268 |
| Ar Flush (min) | 1 | 1 | 1 | 1 | 0 |
| CB (mMole) | 147.3 | 147.3 | 147.3 | 147.3 | 147.3 |
| CB (min) | 12 | 12 | 12 | 12 | 12 |
| Wt. % Conv. | 94.9 | 84.9 | 81.6 | 81.8 | 100.0 |
| Temp. | 160 | 152 | 155 | 157 | 156 |
| Ar. (cc/min) | 100 | 50 | 25 | 10 | 0 |

In example 45, the chlorobenzene and chlorine gas were fed simultaneously with disastrous results (see Table 4B). A very small amount of product was recovered, and it was about 75 percent TCB. We believe that most of the chlorobenzene was converted to tetrachlorobenzene and higher polychlorinated aromatics which remained on the column. The catalyst bed was obviously contaminated so the bath was heated to 180° C. with an argon flush of 100 ml/min for 3 hours to remove higher chlorinated aromatics. The bath temperature was reduced to normal and example 46 was carried out. This resulted in a good P/P+O of 95.8 percent but low conversion (49 percent) and product recovery (47 percent). Example 47, a further check, exhibited the same behavior.

EXAMPLES 48–49

Examples 48 and 49 demonstrate that HCl gas can be used as the carrier or flush gas with no deterioration of the P/P+O ratio (about 95 percent) as shown in Table 4B.

TABLE 4B

| Example No. | 45 | 46 | 47 | 48 | 49 |
|---|---|---|---|---|---|
| | Mole Percent | | | | |
| CB | 0.0 | 14.0 | 46.4 | 53.7 | 44.7 |
| MDCB | 0.0 | 0.3 | 0.0 | 0.0 | 0.0 |
| PDCB | 25.2 | 81.3 | 51.1 | 44.1 | 51.1 |
| ODCB | 0.0 | 4.4 | 2.5 | 2.2 | 2.8 |
| TCB | 74.8 | 0.0 | 0.0 | 0.0 | 1.4 |
| % Conversion | 100.0 | 49.1 | 53.6 | 46.3 | 55.3 |
| P/(P + O) (%) | 100.0 | 95.8 | 95.3 | 95.2 | 94.7 |
| Pro. Rec. Wt. % | 2.4 | 47.0 | 59.7 | 83.2 | 77.8 |
| $Cl_2$ (mMole) | 268 | 134 | 179 | 89 | 89 |
| Ar Flush (min) | 1 | 20 | 10 | 10 | 40 |
| CB (mMole) | 147.3 | 49.1 | 49.1 | 49.1 | 49.1 |
| CB (min) | 30 | 4 | 4 | 4 | 4 |
| Wt. % Conv. | 100.0 | 55.7 | 60.1 | 52.9 | 61.9 |
| Temp. | 155 | 155 | 160 | 157 | 165 |
| Ar. (cc/min) | 25 | 25 | 25 | +HCl | HCl |

Inert gases useful in the present invention include argon, helium, neon, nitrogen, and mixtures thereof. Additionally, HCl produced in the reaction can substitute for part of the inert gas as it does not enter into the reaction. For purposes of the process herein HCl gas although not an inert gas will be defined and treated as an inert gas since it is inert to the reaction. It can be fully substituted for the other inert gases herein. Use of HCl will aid in reducing overall costs. It will be apparent to those skilled in the art that the pulse of inert gas provides several advantages not available in the prior art. First, the pulses of vaporized chlorobenzene are advantageously separated from pulses of chlorine gas. This serves to prevent mixing of the gases and prevents a competing reaction that has lower yield of p-dichlorobenzene. Second, this separation allows the chlorine gas and vaporized chlorobenzene to follow each other in short time periods. Thirdly, the vaporized chlorobenzene or chlorine quantities can be advantageously chosen to provide the optimum reaction conditions. That is, the respective reactions need not continue until all of the $FeCl_3$ has been converted or all of the $FeCl_2$ regenerated to $FeCl_3$. The reactions can occur at the most advantageous process conditions since a pulse of each reactant gas can follow the other, separated only by a relatively short pulse of inert gas. Preferably the pulses of vaporized benzene or chlorobenzene are not present in sufficient quantities to allow the reaction of $FeCl_3$ to $FeCl_2$ to go to completion. Rather, it is contemplated that the pulses of benzene or chlorobenzene are adjusted to allow the reactions to operate at the most advantageous conditions. Thus a sequential pulse of inert gas (without benzene or chlorobenzene) would be applied at least prior to substantially complete reaction of $FeCl_3$ to $FeCl_2$. This is to keep the $FeCl_3$ maximized in order to obtain a high P/O ratio. Fourth, each pulse of inert gas serves to flush any remaining unreacted vaporized chlorobenzene or chlorine gas ahead of it into contact with the catalyst or out the column thus preventing disadvantageous mixing of the gases. Fifth, controlling the pulses of inert gas allows the simultaneous presence and reaction of chlorobenzene with the catalyst and the regeneration of the catalyst with chlorine to occur with the same reactor without mixing of the two reactant gases. Thus, at least part of one or multiple pulses of each reactant gas may be present in the reactor and at least one pulse or multiple of pulses of each reactant may be reacting in the same reactor simultaneously without mixing.

Figure 2:
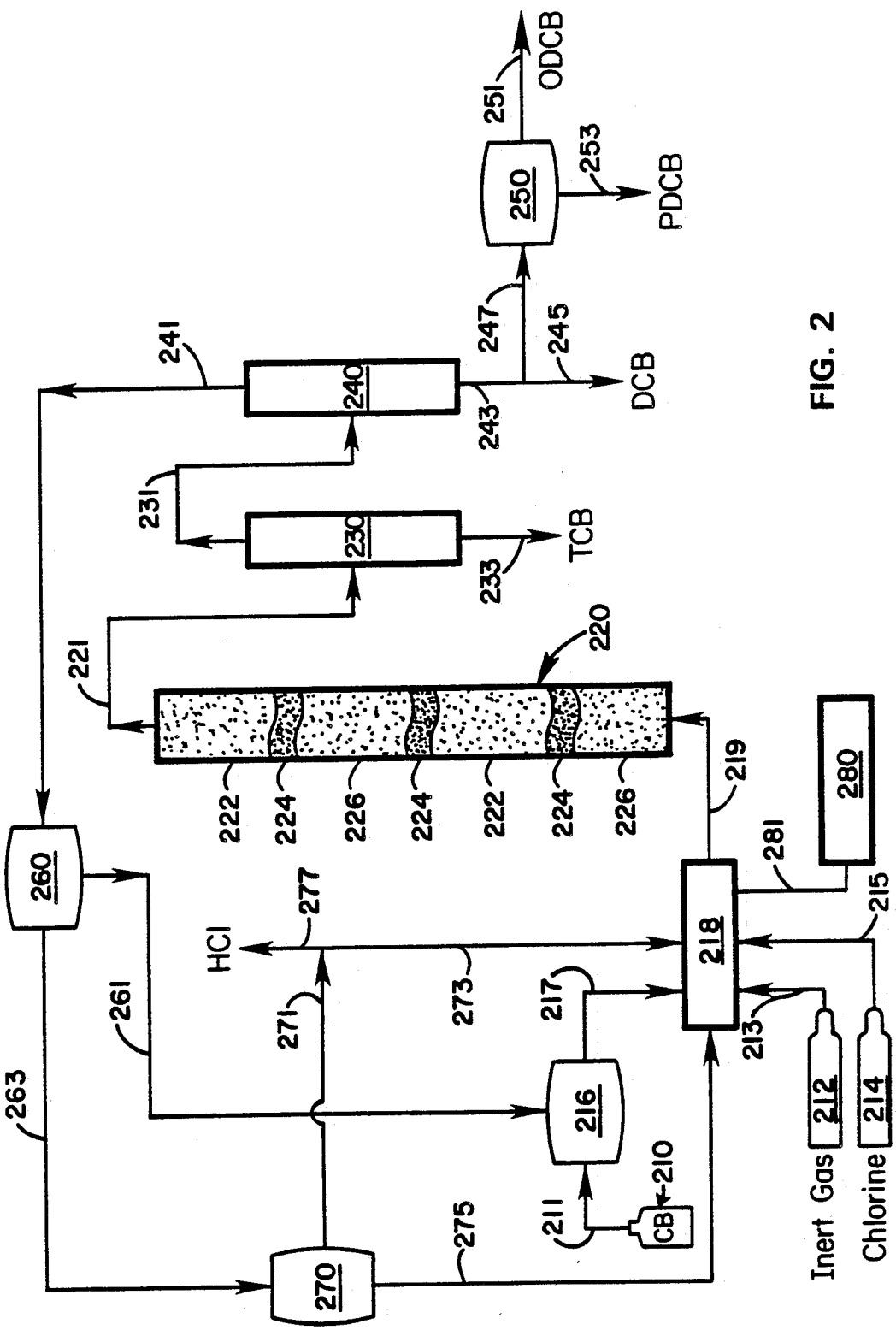
FIG. 2 illustrates an apparatus useful for practicing the invention.

FIG. 2 depicts in flow sheet form an apparatus useful for the improved process of the invention. Gas supply means include inert gas source 212, chlorine source 214, chlorobenzene source 210 and vaporizer 216. The apparatus provides for a source of chlorobenzene 210 that flows as a liquid to evaporator 216 by line 211. Gaseous chlorobenzene from evaporator 216 passes to metering unit 218 by line 217 and then to the input of reaction column 220 by line 219.

Control means comprising metering control 280 and pulse-meter 218 control the flow of gases to the reactor. Metering Control 280 provides appropriate signals to pulse-meter 218 for switching between gases provided at lines 213, 215, 217, 273, and 275 from other gas sources: inert gas 212, chlorine 214, evaporator 216, and scrubber 270 respectively. The gases may be provided in the following sequence for flow through column 220: Chlorobenzene 222, inert gas 224, chlorine 226, and inert gas 224 after which this sequence is repeated. If desired inert gas and/or HCl may be added as a carrier to the chlorobenzene and/or chlorine metered gases to provide a mixture of appropriate concentrations. If needed an initial long pulse of chlorine is provided to activate the catalyst/reagent composition in reactor 220. This is then followed by a pulse of inert gas and then the sequence outlined above.

Reactor means illustrated by reactor column 220 may comprise one or more columns in parallel. Preferably, a reactor column 220 is shaped so as to facilitate the flow of multiple pulses of gases therethrough and to facilitate the distribution of gas as it is introduced to the reactor so that a wavefront of each gas sweeps the previous gas before it. Such a reactor preferably has a length much longer than the width. The diameter of reactor column 220 is in the range of about 2 to about 20 cm to facilitate flow and allow control of reaction temperatures. Preferably, the diameter is about 2 to about 8 cm. A temperature control means (not shown) that is analogous to the oil bath 120 of FIG. 1 may be used. A circulating liquid such as silicone oil, or the like, for keeping the temperature within the desired range is preferred.

Separation means comprising distillation columns 230, 240, stripper 250, condenser 260 and, scrubber 270 separate the product stream from line 221 into constituent components. The separation means may use any appropriate equipment known in the art to accomplish its purpose. The first distillation column 230 separates the output gases containing principally dichlorobenzenes from trichlorobenzene and higher polychlorinated benzenes. Trichlorobenzene and polychlorinated benzenes are removed as residue at line 233. The distillate is introduced via line 231 to a second distillation column 240 where dichlorobenzenes are separated from inert gases, HCl, and unreacted chlorobenzene. Dichlorobenzenes are removed as residue at line 243. The residue may be withdrawn at line 245 or separated further by separator/crystallizer 250 via line 247 to produce separated o-dichlorobenzene and p-dichlorobenzene that can be removed via lines 251 and 253 respectively.

Distillate, from distillation column 240 containing chlorobenzene, gaseous HCl, and inert gas, is removed at line 241 and passes to condenser 260 where chlorobenzene is separated. Separated chlorobenzene can be returned to vaporizer 216 by line 261 for reuse. Inert gases and HCl are piped to scrubber 270 by line 263. Scrubber 270 separates HCl from the inert gas. Inert gas can be recycled to the system by line 275 to pulse meter 218. At least a portion of the HCl can likewise be returned to pulse meter 218 via lines 271 and 273 where it can substitute for a portion of the inert gas in the process. Excess HCl can be removed via line 277.

While chlorobenzene is preferred, benzene may be substituted for chlorobenzene in the method of the invention to produce dichlorobenzene directly. However, conversion percentages and the para/ortho ratio will be affected. Those skilled in the art will recognize the adjustments necessary to use benzene throughout the process once knowing the teachings of the invention. Thus if benzene is used herein, wherever the presently described process requires chlorobenzene it is understood that benzene can be substituted therefor.

Persons skilled in the art will recognize that further optimization of process conditions will provide maximum conversion and efficiency. This optimization can be readily made once knowing the teachings of the invention. For example reactant concentrations; gas flow rates; length of pulse times; temperatures; pressures; selection or catalyst/reagent composition; packing and particle sizes can all be varied to obtain maximum conversion and highest para/ortho ratios.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. A method of producing p-dichlorobenzene comprising:
    a. reacting a pulse of vaporized benzene or chlorobenzene with a catalyst at a temperature between about 100° C. and about 190° C. to convert benzene or chlorobenzene to p-dichlorobenzene, whereby the catalyst is selected from the group consisting of $FeCl_3$, and a mixture of $FeCl_3$ and $AlCl_3$;
    b. providing a pulse of inert gas in an amount sufficient to separate the pulse of vapor in step a from a subsequent pulse of gas and to sweep unreacted vaporized benzene or chlorobenzene, and p-dichlorobenzene from the catalyst;
    c. providing and reacting a pulse of chlorine gas with the catalyst at a temperature between about 100° C. and about 190° C. to reactivate the catalyst;
    providing a pulse of inert gas an amount sufficient to separate the pulse of gas in step c from a subsequent pulse of vapor and to sweep unreacted chlorine gas from the catalyst;
    repeating steps a, b, c, and d sequentially, whereby mixing of the vaporized benzene or chlorobenzene, and the chlorine gas is prevented, and whereby a P/P+O ratio of greater than about 92.3 percent is obtained and less than about 0.2 mole percent trichlorobenzene is formed; and
    f. recovering p-dichlorobenzene.

2. The method of claim 1 further comprising maintaining the reactions at a temperature between about 140° C. and about 175° C.

3. The method of claim 1 further comprising initially reacting the catalyst provided in step a with chlorine so as to activate the catalyst.

4. The method of claim 1 further comprising providing the catalyst deposited on a porous inert substrate.

5. The method of claim 1 further comprising providing the catalyst deposited on a porous inert resilient substrate.

6. The method of claim 5 further comprising providing the catalyst deposited on vermiculite.

7. The method of claim 5 further comprising providing vermiculite having a particle size between about 2 mm and about 6 mm.

8. The method of claim 1 further comprising the additional step of selecting the inert gas from the group consisting of argon, helium, neon, nitrogen, gaseous HCl, and mixtures thereof, prior to providing the inert gas.

9. The method of claim 1 further comprising providing a continuous flow of a second inert gas to the reactor throughout the sequence of steps a, b, c, d, and e where pulses of gas are introduced to the reactor, whereby the second inert gas acts as a carrier.

10. The method of claim 9 further comprising the additional step of selecting the inert gas from the group consisting of argon, helium, neon, nitrogen, gaseous HCl, and mixtures thereof, prior to providing the gas.

11. A method for producing p-dichlorobenzene comprising:
   a. providing a reactor containing a catalyst adapted to convert benzene or chlorobenzene to p-dichlorobenzene, wherein the reactor has an inlet and an outlet for introducing reactants and removing product, whereby the catalyst is selected from the group consisting of $FeCl_3$, and a mixture of $FeCl_3$ and $AlCl_3$, and maintaining the reactor at a temperature between about 100° C. and about 190° C.;
   b. introducing a pulse of vaporized benzene or chlorobenzene into the reactor, and reacting the vapor with the catalyst, whereby p-dichlorbenzene is formed;
   c. introducing a pulse of inert gas into the reactor in an amount sufficient to separate the pulse of gas in step b from a subsequent pulse of gas and to sweep unreacted vaporized benzene or chlorobenzene, and p-dichlorobenzene from the catalyst;
   d. introducing a pulse of chlorine gas into the reactor, and reacting the gas with the catalyst,;
   e. introducing a pulse of inert gas into the reactor in an amount sufficient to separate the pulse of gas in step d from a subsequent pulse of vapor and to sweep unreacted chlorine from the catalyst;
   f. repeating steps b, c, d, and e in a sequential manner, whereby mixing of the vaporized benzene or chlorobenzene, and the chlorine gas is prevented, and whereby a P/P+O ratio of greater than about 92.3 percent is obtained and less than about 0.2 mole percent trichlorobenzene is formed; and
   g. continuously removing product from the outlet of the reactor and recovering p-dichlorobenzene.

12. The method of claim 11 further comprising maintaining the reactor at a temperature between about 140° C. and about 175° C.

13. The method of claim 11 further comprising reacting the catalyst provided in step a with chlorine prior to step b so as to activate the catalyst.

14. The method of claim 11 further comprising providing the catalyst deposited on a porous inert substrate.

15. The method of claim 11 further comprising providing the catalyst deposited on a porous inert resilient substrate.

16. The method of claim 11 further comprising providing the catalyst deposited on vermiculite.

17. The method of claim 11 further comprising providing vermiculite having a particle size between about 2 mm and about 6 mm.

18. The method of claim 11 further comprising selecting an inert gas from the group consisting of argon, helium, neon, nitrogen, gaseous HCl, and mixtures thereof, prior to introducing the gas to the reactor in step c.

19. The method of claim 11 further comprising introducing a continuous flow of a second inert gas as a carrier to the reactor throughout the sequence of steps b, c, d, e and f where pulses of gas are introduced to the reactor, whereby the second inert gas acts as a carrier.

20. The method of claim 19 further comprising selecting the continuous flow of inert gas from the group consisting of argon, helium, neon, nitrogen, gaseous HCl, and mixtures thereof.

21. The method of claim 11 further comprising controlling the introduction of the pulses to provide for the simultaneous presence in the reactor of at least part of a pulse of vaporized benzene or chlorobenzene with at least part of a pulse of chlorine gas, whereby the pulses are separated from each other by a pulse of inert gas.

22. The method of claim 11 further comprising controlling the introduction of the pulses to provide for the simultaneous presence in the reactor of multiple sequential pulses of vaporized benzene or chlorobenzene, and chlorine gas, whereby each pulse is separated by a pulse of inert gas from the other pulses.

* * * * *

UNITED STATES PATENT AND TRADEMARK OFFICE
CERTIFICATE OF CORRECTION

PATENT NO. : 5,001,290
DATED : March 19, 1991
INVENTOR(S) : Melville Hillman, James D. Browning It is certified that error appears in the above-indentified patent and that said Letters Patent is hereby corrected as shown below:

Column 6, line 45, delete "2B" insert —1B—

Column 8, line 12, delete "66 2" insert —66.2—

Column 12, line 45, delete "80" insert —80-81—

Column 16, line 33, "It will ..." begins a new paragraph

Column 18, line 55, before "providing" at the beginning of the line insert —d.—

Column 18, line 59, before "repeating" at the beginning of the line insert —e.—

Column 19, line 45, second line of step c., delete "gas" insert —vapor—

Signed and Sealed this

First Day of March, 1994

Attest:

BRUCE LEHMAN

*Attesting Officer*  *Commissioner of Patents and Trademarks*